United States Patent
Habara et al.

[11] Patent Number: 5,855,586
[45] Date of Patent: Jan. 5, 1999

[54] MEDICAL LIGATURE ENABLING RELIABLE LIGATION IRRESPECTIVE OF OPERATOR'S EXPERTISE

[75] Inventors: Koji Habara, Higashiyamato; Koichiro Saito, Hachioji, both of Japan

[73] Assignee: Olympus Optical Co. Ltd., Tokyo, Japan

[21] Appl. No.: 801,292

[22] Filed: Feb. 18, 1997

[30] Foreign Application Priority Data

Apr. 17, 1996 [JP] Japan .................................... 8-095533
Nov. 6, 1996 [JP] Japan .................................... 8-294146

[51] Int. Cl.⁶ .................................................. A61B 17/04
[52] U.S. Cl. ........................ 606/144; 606/157; 606/151; 606/139
[58] Field of Search ..................... 609/144, 151, 609/139, 140, 141, 157, 158, 120

[56] References Cited

U.S. PATENT DOCUMENTS

| | | | |
|---|---|---|---|
| 3,476,114 | 11/1969 | Shannon et al. | 606/139 |
| 3,985,138 | 10/1976 | Jarvik | 128/326 |
| 4,018,229 | 4/1977 | Komiya | 128/326 |
| 4,069,825 | 1/1978 | Akiyama | 128/335.5 |
| 5,383,905 | 1/1995 | Golds et al. | 606/232 |
| 5,501,692 | 3/1996 | Riza | 606/148 |
| 5,643,295 | 7/1997 | Yoon | 606/151 |

FOREIGN PATENT DOCUMENTS 23 08 846 C 3  8/1973  Germany.

Primary Examiner—Michael Buiz
Assistant Examiner—Tina T. D. Pham
Attorney, Agent, or Firm—Armstrong, Westerman, Hattori, McLeland & Naughton

[57] ABSTRACT

A ligature comprises a ligation loop located on the distal side of the ligature, a stopper through which the ligation loop is passed in a united state, a hooked loop located proximally of the stopper, and a restriction member formed so that a plasto-elastic wire forming the ligation loop can penetrate through the restriction member. The ligation loop and hooked loop are formed with plasto-elastic wires made of a synthetic resin. The cylindrical stopper is press-fitted on the part of the ligation loop folded in two, and the hooked loop is formed behind the stopper. The ligation loop is provided with the restriction member formed with a plasto-elastic tubular member with the wire of the ligation loop passed through the restriction member.

11 Claims, 5 Drawing Sheets

MEDICAL LIGATURE ENABLING RELIABLE LIGATION IRRESPECTIVE OF OPERATOR'S EXPERTISE

BACKGROUND OF THE INVENTION

1. Field of the Invention

The present invention relates to a medical ligature for ligating the tissue of a lesion inside a human body.

2. Description of the Related Art

In the past, there has been a medical ligature for ligating the tissue of a lesion in a human body trans-endoscopically, that is, by inserting the medical ligature into the human body through a therapeutic instrument insertion channel in an endoscope.

This kind of medical ligature is such that a wire made of a synthetic resin is looped to form a ligation loop on the distal side of the ligature, and the ligation loop is used to ligate the tissue of a lesion and indwelled intact in the human body for several days. As a result, a blood flow through the tissue of the lesion is arrested owing to the ligation. The tissue of the lesion therefore necroses several days later and drops. At this time, the medical ligature also drops and is excreted naturally through the anus.

In the foregoing known medical ligature, the ligation loop is used to ligate the tissue of a lesion, and a stopper is moved toward the distal end of the ligation loop in order to make the ligature loop smaller and thus ligate the tissue of the lesion with the ligation loop. At this time, since no member is provided for restricting the movement of the stopper, the ligation loop can assume any size during ligation and can be made unlimitedly small in terms of the structure. This means that adjusting the strength of ligation depends solely on the extent of an operator's force in practical use, and poses a problem that the efficacy of treatment varies depending on operator's expertise.

OBJECTS AND SUMMARY OF THE INVENTION

An object of the present invention is to provide a medical ligature enabling reliable ligation irrespective of operator's expertise despite a simple structure.

Another object of the present invention is to provide an inexpensive medical ligature with a simple structure.

A medical ligature of the present invention comprises a ligation loop formed of a plasto-elastic wire, a cylindrical stopper press-fitted on the ligation loop with the plasto-elastic wire of the ligation loop united, a hooked loop located proximally of the stopper and capable of being hooked by a towing hook so that it can be unhooked from the towing hook freely, and a restriction member, formed between the distal end of the ligation loop and the stopper, for restricting the movement of the stopper toward the distal end.

Other features and advantages of the present invention will be fully apparent from the description below.

BRIEF DESCRIPTION OF THE DRAWINGS

FIG. 1 shows the structure of a medical ligation apparatus. FIG. 2 is an explanatory diagram for explaining the operation of a ligature included in the medical ligation apparatus shown in FIG. 1. FIG. 3 shows the structure of the first variant of the ligature shown in FIG. 1, and FIG. 4 shows the structure of the second variant of the ligature shown in FIG. 1.

FIG. 6 shows the structure of a medical ligation apparatus, and FIG. 7 shows the structure of a ligature included in the apparatus shown in FIG. 6.

FIG. 8 shows the structure of a ligature included in a medical ligation apparatus. FIG. 9 is a sectional view showing a section A—A of the ligature shown in FIG. 8, and FIG. 10 is an explanatory diagram for explaining the kinds of restriction members, one of which is shown in FIG. 8.

FIG. 12 shows the structure of a ligature included in a medical ligation apparatus. FIG. 13 shows a section B—B of FIG. 12, and FIG. 14 is an explanatory diagram for explaining the operation of the ligature shown in FIG. 12.

DETAILED DESCRIPTION OF THE PREFERRED EMBODIMENTS

First Embodiment

Figure 1:
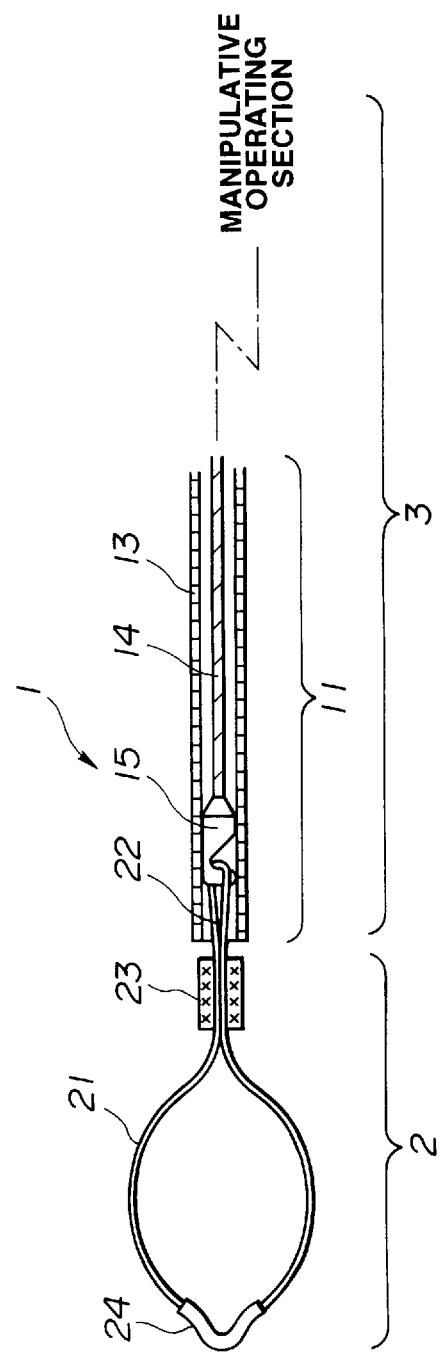
FIGS. 1 to 4 relate to the first embodiment of the present invention.

As shown in FIG. 1, a medical ligation apparatus 1 in accordance with this embodiment comprises a ligature 2 to be indwelled in a human body, and an operation unit 3 for introducing the ligature 2 into the human body for ligation.

The operation unit 3 includes an inserting section 11 and a manipulative operating section (not shown). The main inserting section 11 includes a sheath 13, and an operation wire 14 inserted into the lumen of the sheath 13 so that the operation wire can advance or withdraw. A hook 15, which is shaped like a fish hook, for locking the ligature 2 so that the ligature 2 can be detached freely, is attached to the tip of the operation wire 14.

The hook 15 has an outer diameter permitting the hook 15 to be freely led into the sheath 13. When led into the sheath 13, the hook 15 has an opening around a hooking part thereof walled up within the inner surface of the sheath 13.

Next, the structure of the ligature 2 will be described. The ligature 2 includes a ligation loop 21 located on the distal side of the ligature 2, a stopper 23 into which the ligation loop 21 is inserted in a united state, a hooked loop 22 located proximally of the stopper 23, and a restriction member 24 shaped so that the plasto-elastic wire forming the ligation loop 21 can penetrate through the restriction member. The ligation loop 21 and hooked loop 22 are formed up plasto-elastic wires made of a synthetic resin, for example, nylon or polyolefine, or a metal, for example, stainless steel.

In other words, the cylindrical stopper 23 is press-fitted on part of the ligation loop 21 folded in two. The hooked loop 22 is formed behind the stopper 23. The ligation loop 21 is provided with the restriction member 24 which is formed with a plasto-elastic tubular member, for example, a tube made from a synthetic resin, such as polyolefine or fluoro-carbon resin, or with a metallic plasto-elastic hollow structure, such as a coil or spiral tube, and through which the wire forming the ligation loop 21 is lying.

The operation of the medical ligation apparatus 1 in accordance with this embodiment having the foregoing components will be described.

First, as shown in FIG. 1, the hook 15 is hung on the hooked loop 22 of the ligature 2. In this state, the hooked loop 22 is led into the sheath 13. The ligation loop 21 is then hung on an intended lesion. The hook 15 is withdrawn by manipulating the manipulative operating section 12. The ligature 2 is then led into the sheath 13 by way of the hook 15. However, since the back end of the stopper 23 abuts the distal end of the sheath 13, only the plasto-elastic wire of the ligature 2 is led into the sheath. The ligation loop 21 is therefore constricted until the restriction member abuts against the stopper 23. Consequently, the tissue of the lesion is ligated.

Thereafter, the hook 15 is jutted out from the distal end of the sheath 13 again. The hooked loop 22 then comes off from the hook 15, and the ligature 2 alone is indwelled in the body.

Thus, constricting and tying the tissue of a lesion in a human body is completed.

Figure 2:
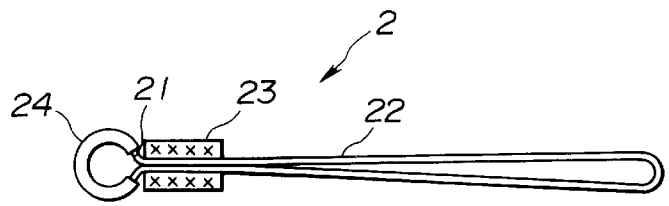

As mentioned above, the medical ligation apparatus 1 in accordance with this embodiment enables reliable ligation irrespective of operator's expertise because, as shown in FIG. 2, the restriction member 24 makes it possible to restrict the size of a ligation loop to a given size for the purpose of constricting and tying the tissue of a lesion (not shown).

The ligature 2 includes the restriction member 24 formed with a plasto-elastic tubular member, for example, a tube made of a synthetic resin, such as polyolefine or fluorocarbon resin, or a metallic plasto-elastic hollow structure, such as a coil or spiral tube. The structure of the ligature is not limited to this one. Alternatively, the ligature may have a structure described below. A medical ligation apparatus including the ligature with this structure can still provide the same operation and advantage as the aforesaid medical ligation apparatus 1.

Figure 3:
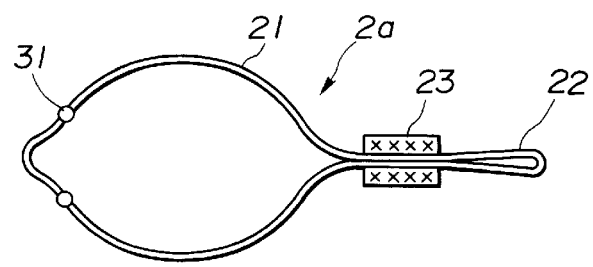

Specifically, a ligature 2a of the first variant may be, as shown in FIG. 3, a ligature provided with a restriction member 31 composed of bosses, which are spherical parts made of the same resin as the ligation loop 21 so that the plasto-elastic wire of the ligation loop 21 can penetrate through the spherical parts, or which are spherical members being made of a synthetic resin or metal and having a bore through which the ligation loop 21 can pass.

Figure 4:
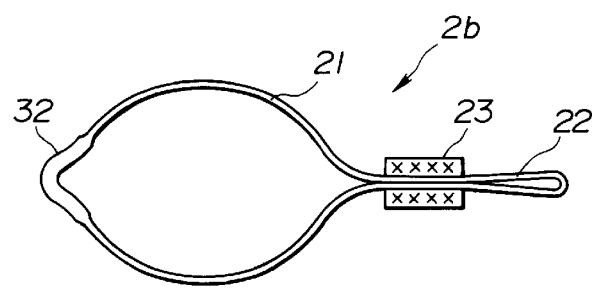

Alternatively, as a ligature 2b of the second variant may be, as shown in FIG. 4, a ligature provided with a restriction member 32 made by making the diameter of part of the wire of the ligation loop 21, which maintains the shape of a loop during constriction and tying, larger than that of the other part.

Second Embodiment

The second embodiment is nearly identical to the first embodiment. Only a difference will be described. Components identical to those in the first embodiment are assigned the same reference numerals. The description of the components will be omitted.

Figure 5:
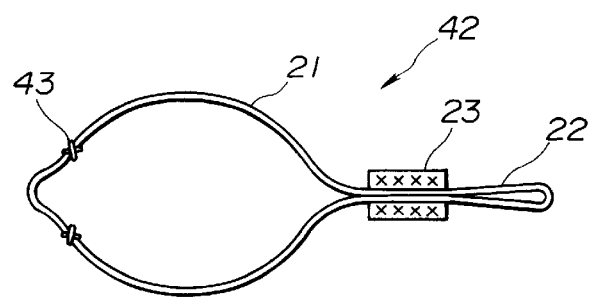
FIG. 5 shows the structure of a ligature included in a medical ligation apparatus in accordance with the second embodiment of the present invention.

In a ligature 42 included in a medical ligation apparatus in accordance with the second embodiment, the ligation loop 21 is, as shown in FIG. 5, provided with a restriction member 43 composed of bosses that are, for example, knots of the ligation loop 21.

The other components of the second embodiment and the operation thereof are identical to those of the first embodiment.

Thus, this embodiment provides the same advantage as the one provided by the first embodiment and its variants. In addition, since the restriction member 43 is composed of the bosses that are knots of the ligation loop 21, an inexpensive ligature can be constructed.

Third Embodiment

The third embodiment is nearly identical to the first embodiment. Only a difference will be described. Components identical to those in the first embodiment are assigned the same reference numerals. The description of the components will be omitted.

Figure 6:
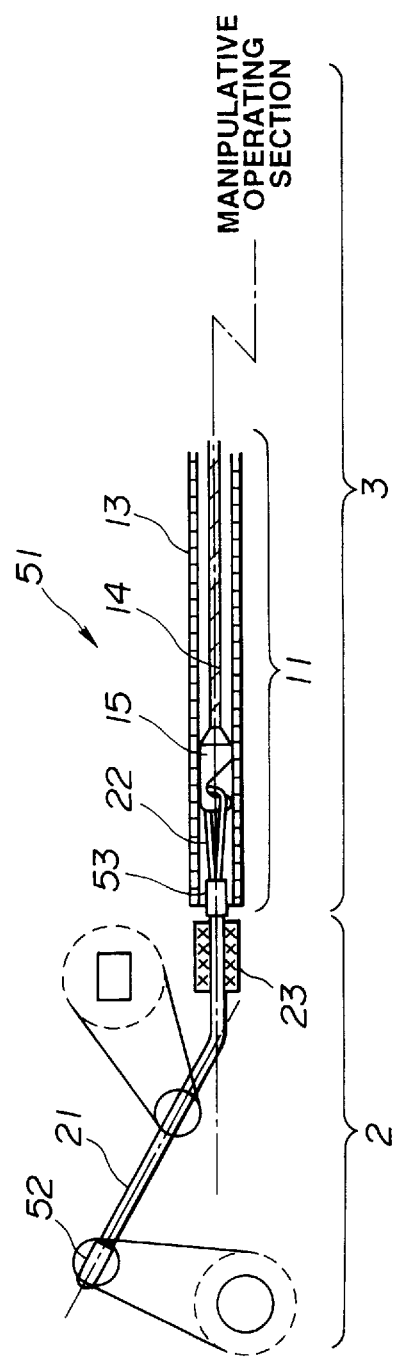
FIGS. 6 and 7 relate to the third embodiment.

In a medical ligation apparatus 51 of this embodiment, as shown in FIG. 6, the section of the proximal part of the wire of the ligation loop 21 is shaped like a rectangle thinner than that of an insertion bore of the stopper 23. The section of the distal part of the wire which maintains the shape of a loop during constriction and tying is shaped like a circle wider than the insertion bore of the stopper 23. A restriction member 52 is thus formed by differentiating the sectional shape of the ligation loop 21 between the proximal and distal parts of the wire. The center line of the ligation loop 21 is aligned with the center line of the inserting section 11 at an angle.

Figure 7:
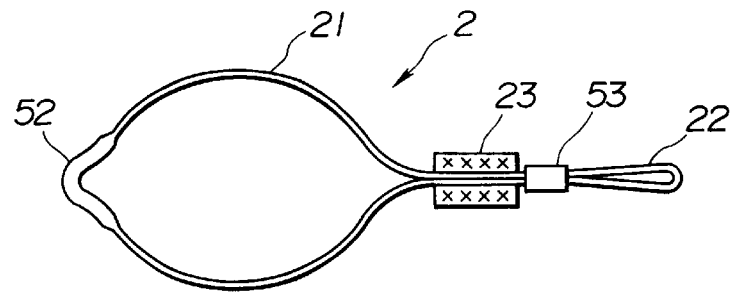

The ligation loop 21 and hooked loop 22 are formed of different plasto-elastic wires, and, as shown in FIG. 7, joined with each other within a cylindrical joint member 53, which is made of, for example, a synthetic resin such as polyolefine or fluorocarbon resin or a metal such as stainless steel, by means of an adhesive, caulking, soldering, brazing, or the like.

The other components of the third embodiment and the operation thereof are identical to those of the first embodiment.

Thus, this embodiment provides the same advantage as the one of the first embodiment and its variants. In addition, since the whole ligation loop 21 is formed of a band-like wire, the ligation loop 21 can be constructed as a ligation loop having stronger rigidity against bending in a specified direction. Moreover, since the center line of the ligation loop 21 is aligned with the center line of the inserting section 11 at an angle, the ligation loop 21 can easily be hung on the tissue of a lesion on an internal wall of a body cavity resting nearly perpendicularly to the center line of the inserting section 11.

Fourth Embodiment

The fourth embodiment is nearly identical to the first embodiment. Only a difference will be described. Components identical to those of the first embodiment are assigned the same reference numerals. The description of the components will be omitted.

Figure 8:
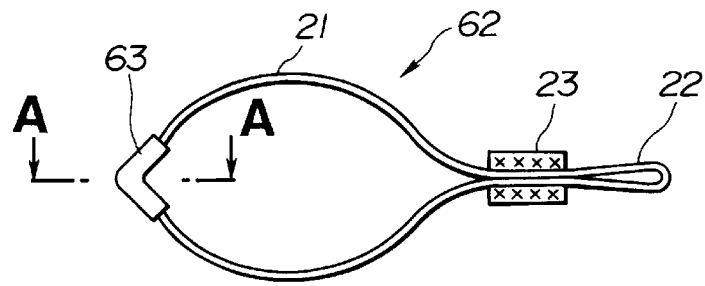
FIGS. 8 to 10 relate to the fourth embodiment.
Figure 9:
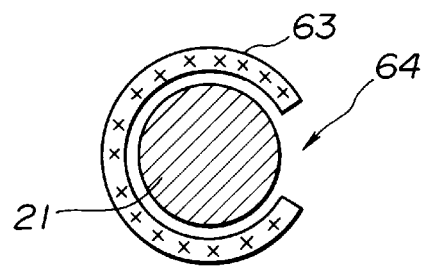
Figure 10:
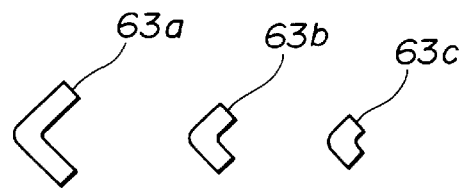

As shown in FIG. 8, a ligature 62 of this embodiment has a restriction member 63 over the distal part of the ligation loop 21. As shown in FIG. 9 that is the A—A sectional view of FIG. 8, the restriction member 63 has an opening 64. The restriction member 63 is, as shown in FIG. 10, selected from among a plurality of restriction members 63a, 63b, and 63c (three kinds of restriction members in FIG. 10) having different lengths. Any of the restriction members 63a, 63b, and 63c is selected and fitted on the ligation loop 21 through the opening 64 thereof so that the selected restriction member can be detached freely.

The restriction member 63 having a desired length is fitted on the distal part of the ligation loop 21 prior to use.

The other components of the fourth embodiment and the operation thereof are identical to those of the first embodiment.

Thus, this embodiment can provide the same advantage as the one of the first embodiment and its variants. In addition, since a plurality of restriction members can be used as the restriction member 63, the diameter of a loop formed by the ligation loop 21 after ligation can be varied if necessary. Consequently, lesions of various sizes can be dealt with.

Fifth Embodiment

The fifth embodiment is nearly identical to the first embodiment. Only a difference will be described. Components identical to those of the first embodiment are assigned the same reference numerals. The description of the components will be omitted.

Figure 11:
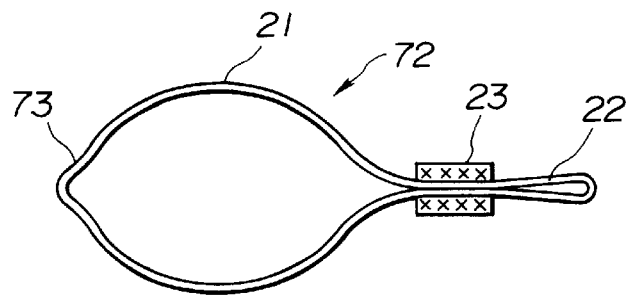
FIG. 11 shows the structure of a ligature included in a medical ligation apparatus in accordance with the fifth embodiment of the present invention.

As shown in FIG. 11, a ligature 72 of this embodiment has a restriction member 73 formed by roughing the surface of the distal part of the ligation loop 21 to make the surface irregular, and thus making the coefficient of friction of the distal part higher than that of the other part of the ligation loop 21. The movement of the stopper 23 is restricted by a frictional force occurring between the inner surface of the stopper 23 and the face of the restriction member 73.

The other components of the fifth embodiment and the operation thereof are identical to those of the first embodiment.

Thus, this embodiment can provide the same advantage as the one of the first embodiment and its variants. In addition, since the restriction member 73 is formed by roughing the surface of the distal part of the ligation loop 21. An inexpensive ligature can be constructed.

Sixth Embodiment

Figure 12:
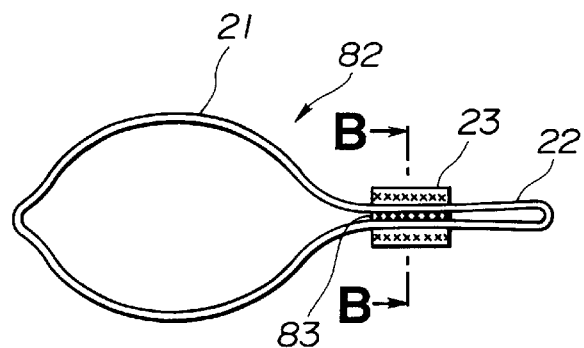
FIGS. 12 to 14 relate to the sixth embodiment of the present invention.
Figure 13:
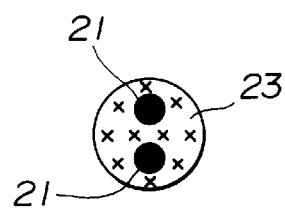
Figure 14:

As shown in FIG. 12, in a ligature 82 of this embodiment, the stopper 23 is a two-lumen tube shown in FIG. 13. The tip of the stopper 23 acts as a restriction tip 83. As shown in FIG. 14, the movement of the stopper 23 is restricted by the restriction tip 83 formed on the stopper 23 that abuts against the distal end of the ligation loop 21.

The other components of the sixth embodiment and the operation and advantage thereof are identical to those of the first embodiment.

In the present invention, it is apparent that a wide range of different embodiments can be constituted on the basis of the invention without departure from the sprit and scope of the invention. This invention will be limited to the appended claims but not be restricted to any specific embodiment.

What is claimed is:

1. A medical ligature, comprising:

a generally annular body of plasto-elastic wire, a stopper press-fitted about said wire body to bundle segments of said wire at an intermediate position of said body to define a ligation loop on a distal side of said stopper wherein said wire segments are disposed to be located each on opposite sides of a lesion to be ligated and cooperate to form a loop operative to encircle said lesion to be ligated, and a hooked loop on a proximal side of said stopper operative to be releasably hooked by a towing hook, a restriction member disposed substantially on a distal part of said ligation loop comprising means forming obstructions on said wire segments at said distal end of said ligation loop, said stopper being movable along said wire segments to vary the relative size of said ligation loop with respect to said hooked loop thereby to constrict said litigation encircling said lesion to be ligated, and said obstructions of said restriction member being operative to abut said stopper for restricting excessive movement of said stopper toward said distal end of said ligation loop whereby excessive constriction of said ligation loop is prevented.

2. A medical ligature according to claim 1, wherein said restriction member is a plasto-elastic tube through which the plasto-elastic wire of said ligation loop is passed and the ends of said tubes forming said obstructions.

3. A medical ligature according to claim 1, wherein said restriction member includes bosses defining obstructions formed on the plasto-elastic wire of said ligation loop.

4. A medical ligature according to claim 1, wherein said restriction member is selected from among a plurality of restriction members having different lengths and fitting on the distal part of said ligation loop so that it can be detached freely.

5. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop, for restricting the movement of said stopper toward the distal end of said ligation loop, wherein the size of said ligation loop can be reduced by moving said stopper toward the distal end of said ligation loop until it collides with said restriction member; and wherein said restriction member includes knots of the plasto-elastic wire of said ligation loop.

6. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop for restricting the movement of said stopper toward the distal end of said ligation loop, wherein the size of said ligation loop can be reduced by moving said stopper toward the distal end of said ligation loop until it collides with said restriction member; and wherein said restriction member is formed by varying the outer diameter of the plasto-elastic wire of said ligation loop.

7. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop, for restricting the movement of said stopper toward the distal end of said ligation loop, wherein the size of said ligation loop can be reduced by moving said stopper toward the distal end of said ligation loop until it collides with said restriction member; and wherein said restriction member is formed by varying the sectional shape of the plasto-elastic wire forming said ligation loop is shaped like a flat band.

8. A medical ligature according to claim 7, wherein part of the plasto-elastic wire forming said ligation loop is shaped like a flat band.

9. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop, for restricting the movement of said stopper toward the distal end of said ligation loop, wherein the size of said ligation loop can be reduced by moving said stopper toward the distal end of said ligation loop until it collides with said restriction member; and wherein said restriction member is formed by making the coefficient of friction of the surface of the distal part of the plasto-elastic wire of said litigation loop higher than that of the surface of the outer part thereof.

10. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop, for restricting the movement of said stopper toward the distal end of said ligation loop, wherein the size of said ligation loop can be reduced by moving said stopper toward the distal end of said ligation loop until it collides with said restriction member; and wherein at least part of said ligation loop is formed at an angle with respect to said hooked loop.

11. A medical ligature comprising:

a litigation loop formed with a plasto-elastic wire;

a stopper press-fitted on said ligation loop with the wire of said ligation loop united, and enabled to slide on said ligation loop;

a hooked loop formed proximally of said stopper and continuously to the wire of said ligation loop, and capable of being hooked by a towing hook so that it can freely be unhooked from the towing hook;

a restriction member, located at the distal end of said ligation loop, for restricting the movement of said stopper toward the distal end of said ligation loop, wherein the size of said ligation loop can be reduced by moving said stopper toward the distal end of said ligation loop until it collides with said restriction member; and including an operation unit for operating said medical ligature, said operation unit comprising a plasto-elastic sheath, an operation wire inserted into said plasto-elastic sheath through a manipulative operating section, and a towing hook attached to the tip of said operation wire; and said stopper being sized with respect to said sheath to abut against the front end thereof when said hook loop is led into said plasto-elastic sheath.

* * * * *